United States Patent
Konishi et al.

(10) Patent No.: US 9,998,635 B2
(45) Date of Patent: Jun. 12, 2018

(54) ENDOSCOPE SYSTEM

(71) Applicant: OLYMPUS CORPORATION, Tokyo (JP)

(72) Inventors: Jun Konishi, Hachioji (JP); Saeri Saito, Sagamihara (JP); Takeshi Urasaki, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/479,503

(22) Filed: Apr. 5, 2017

(65) Prior Publication Data

US 2017/0208224 A1    Jul. 20, 2017

Related U.S. Application Data (63) Continuation of application No. PCT/JP2016/068245, filed on Jun. 20, 2016.

(30) Foreign Application Priority Data

Jun. 29, 2015    (JP) ................. 2015-130126

(51) Int. Cl.
   *H04N 5/217*      (2011.01)
   *A61B 1/00*      (2006.01)
   (Continued)

(52) U.S. Cl.
   CPC ........... *H04N 5/217* (2013.01); *A61B 1/0002* (2013.01); *A61B 1/00009* (2013.01);
   (Continued)

(58) Field of Classification Search
   CPC ........... H04N 2005/2255; H04N 5/217; H04N 5/2256; A61B 1/00009; A61B 1/00039;
   (Continued)

(56) References Cited

U.S. PATENT DOCUMENTS

| | | | |
|---|---|---|---|
| 4,951,135 A | 8/1990 | Sasagawa et al. | |
| 2002/0188174 A1* | 12/2002 | Aizawa | A61B 1/00059 600/118 |
| 2009/0244271 A1* | 10/2009 | Abe | A61B 1/00009 348/65 |

FOREIGN PATENT DOCUMENTS

| | | |
|---|---|---|
| JP | H01-270842 A | 10/1989 |
| JP | H01-297043 A | 11/1989 |
| | (Continued) | |

OTHER PUBLICATIONS

International Search Report dated Sep. 6, 2016 issued in PCT/JP2016/068245.

*Primary Examiner* — Nathnael Aynalem
(74) *Attorney, Agent, or Firm* — Scully, Scott, Murphy & Presser, P.C.

(57) ABSTRACT

An endoscope system includes: an endoscope including an image pickup device; an EEPROM provided in the endoscope, and configured to hold data according to a kind of the image pickup device; a video processor to which the endoscope is attachably and detachably connected; a control portion provided in the video processor, and configured to acquire the data from the EEPROM when the endoscope is connected to the video processor and set processing content of noise reduction processing, based on the acquired data; and an NR processing circuit provided in the video processor, and configured to execute the noise reduction processing on a video signal outputted from the image pickup device, based on setting of the control portion. The control portion sets execution/non-execution of the noise reduction processing to the NR processing circuit, based on the acquired data.

3 Claims, 5 Drawing Sheets

(51) Int. Cl.
   *A61B 1/04*    (2006.01)
   *A61B 1/233*   (2006.01)
   *A61B 1/07*    (2006.01)
   *G02B 23/24*   (2006.01)
   *H04N 5/225*   (2006.01)

(52) U.S. Cl.
   CPC ...... *A61B 1/00059* (2013.01); *A61B 1/00105* (2013.01); *A61B 1/00124* (2013.01); *A61B 1/04* (2013.01); *A61B 1/07* (2013.01); *G02B 23/2484* (2013.01); *H04N 5/2256* (2013.01); *H04N 2005/2255* (2013.01)

(58) Field of Classification Search
   CPC .............. A61B 1/0002; A61B 1/00059; A61B 1/00105; A61B 1/00124; A61B 1/04; A61B 1/07; A61B 1/045; G02B 23/2484
   See application file for complete search history.

(56) References Cited

FOREIGN PATENT DOCUMENTS

| | | |
|---|---|---|
| JP | H05-329101 A | 12/1993 |
| JP | 2009-195461 A | 9/2009 |
| JP | 2009-279213 A | 12/2009 |
| JP | 2012-017735 A | 1/2012 |

\* cited by examiner

ENDOSCOPE SYSTEM

CROSS REFERENCE TO RELATED APPLICATION

This application is a continuation application of PCT/JP2016/068245 filed on Jun. 20, 2016 and claims benefit of Japanese Application No. 2015-130126 filed in Japan on Jun. 29, 2015, the entire contents of which are incorporated herein by this reference.

BACKGROUND OF THE INVENTION

1. Field of the Invention

The present invention relates to an endoscope system.

2. Description of the Related Art

Conventionally, an endoscope system including an endoscope configured to pick up an image of an object inside a subject, a video processor configured to generate an observation image of the object, the image of which is picked up by the endoscope, and a monitor configured to display the observation image generated by the video processor has been widely used in a medical field, an industrial field, and the like.

In such an endoscope system, in order to reduce noise of an endoscope image, a noise reduction processing function is provided inside the video processor. Since the noise of the endoscope image depends on a performance of an image pickup device loaded on the endoscope, strength of noise reduction needs to be adjusted according to a characteristic of the image pickup device.

For example, Japanese Patent Application Laid-Open Publication No. 2012-17735 discloses an endoscope system including a noise reduction circuit configured to change noise reduction strength according to a gain correction value multiplied with video signals. The noise reduction circuit performs processing of increasing the noise reduction strength in a case where the gain correction value is larger than 1, and lowering the noise reduction strength in the case where the gain correction value is smaller than 1.

SUMMARY OF THE INVENTION

An endoscope system of one aspect of the present invention includes: an endoscope including an image pickup device configured to pick up an image of a subject; a data holding portion provided in the endoscope, and configured to hold data according to a kind of the image pickup device; a signal processor to which the endoscope is attachably and detachably connected; a data acquisition portion provided in the signal processor, and configured to acquire the data from the data holding portion when the endoscope is connected to the signal processor; a noise reduction processing setting portion provided in the signal processor, and configured to set processing content of noise reduction processing, based on the data acquired by the data acquisition portion; and a noise reduction processing portion provided in the signal processor, and configured to execute the noise reduction processing on a video signal outputted from the image pickup device, based on setting of the noise reduction processing setting portion, and the noise reduction processing setting portion sets execution/non-execution of the noise reduction processing to the noise reduction processing portion, based on the data acquired by the data acquisition portion.

BRIEF DESCRIPTION OF THE DRAWINGS

FIG. 5 is a diagram for describing one example of a scope ID stored in an EEPROM 16a; and FIG. 6 is a diagram for describing one example of setting information on NR stored in a table 26a.

DETAILED DESCRIPTION OF THE PREFERRED EMBODIMENTS

Hereinafter, embodiments of the present invention will be described with reference to the drawings.

First Embodiment

Figure 1:
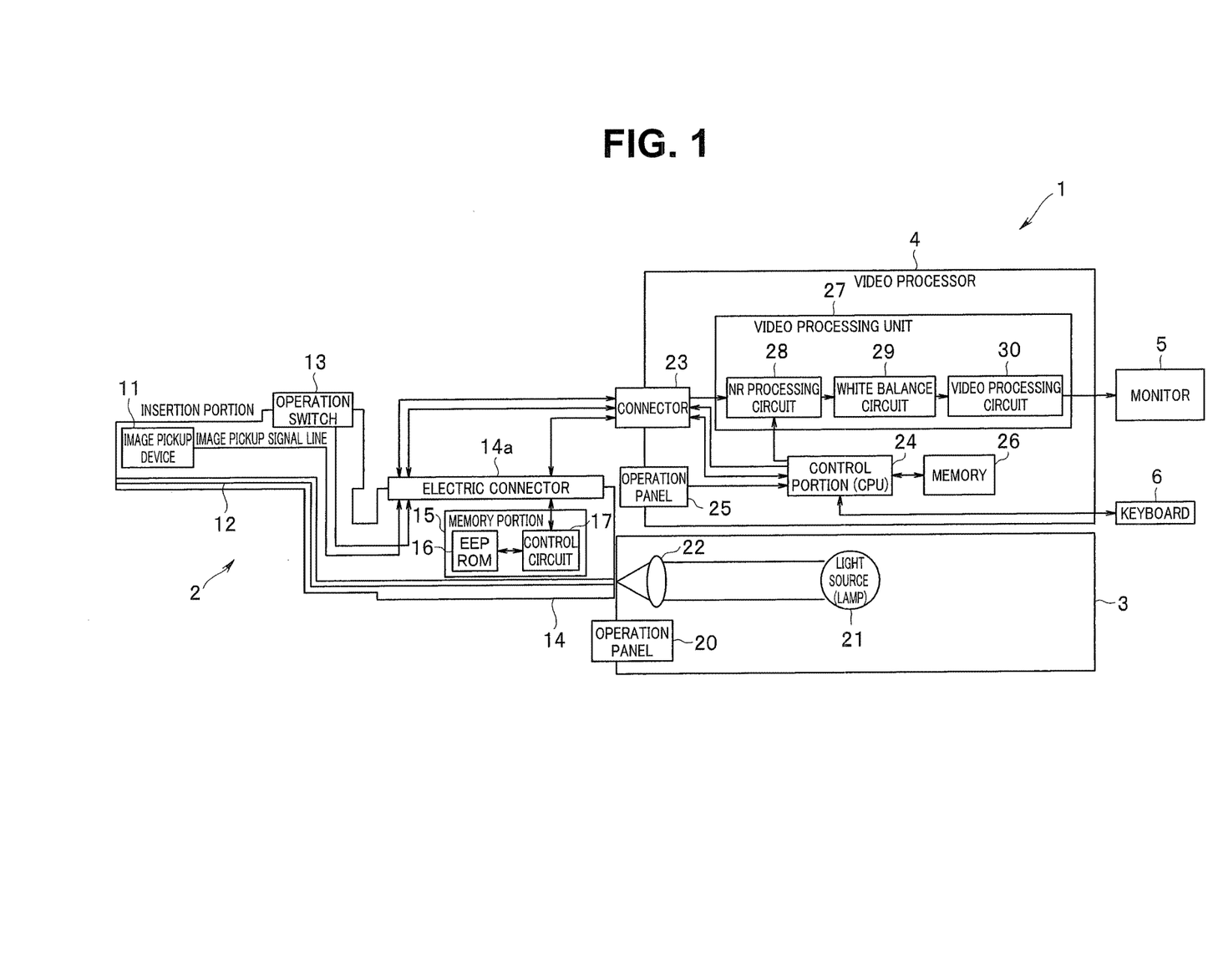
FIG. 1 is a diagram illustrating a configuration of an endoscope system relating to a first embodiment.

First, a configuration of an endoscope system of a first embodiment will be described using FIG. 1. FIG. 1 is a diagram illustrating the configuration of the endoscope system relating to the first embodiment.

As illustrated in FIG. 1, an endoscope system 1 is configured including an endoscope 2 configured to be inserted into a body cavity and observe or treat a lesion, a light source device 3 configured to supply illumination light to the endoscope 2, and a video processor 4 configured to execute predetermined signal processing on a video signal for which an image is picked up by the endoscope 2. To the video processor 4, a monitor 5 configured to display video to which the signal processing is executed, and a keyboard 6 for inputting an operation instruction and character information or the like are connected. Note that, in the endoscope system 1 of the present embodiment, the light source device 3 and the video processor 4 are configured as separate bodies, however, without being limited to the separate bodies, the light source device 3 and the video processor 4 may be integrally configured.

The endoscope 2 includes an image pickup device 11 such as a CCD provided on an insertion portion distal end to be inserted into a body cavity of a patient, a light guide 12 configured to guide the illumination light to the insertion portion distal end, an operation switch 13 provided in an operation portion configured to operate the endoscope 2, an electric connector 14a provided in a connector portion 14 for connection with the video processor 4, and a memory portion 15 in which various kinds of information (scope ID) of the endoscope 2 are stored.

Note that an insertion portion of the endoscope 2 may be flexible or may be rigid (a rigid endoscope used in a surgery). In addition, the image pickup device 11 is provided on the insertion portion distal end of the endoscope 2, but is not limited to the insertion portion distal end. For example, the configuration may be such that the image pickup device 11 is provided inside the operation portion (a portion to be gripped by a user) provided with the operation switch 13, and an optical image is transmitted from the insertion portion distal end to the image pickup device 11 inside the operation portion by an image guide fiber.

Furthermore, in the present embodiment, the video processor 4 is configured such that the endoscope 2 is connected, but is not limited to the configuration, and may be configured such that a camera head mounted on an eyepiece portion of an optical type endoscope (a fiber scope or an optical visual tube for a surgery) to be inserted into the body cavity is connected.

Further, in the present embodiment, the endoscope 2 and the video processor 4 are connected by the electric connector 14a and a connector 23 and configured to transmit electric signals by a wire, but are not limited to the configuration, and may be configured to transmit the electric signals wirelessly.

The memory portion 15 is configured including an EEPROM 16 in which the scope ID of the endoscope 2 is rewritably stored, and a control circuit 17 configured to communicate with a control portion 24 of the video processor 4 to be described later and transmit the scope ID read from the EEPROM 16 to the control portion 24.

Note that, in the present embodiment, the EEPROM 16 in which the scope ID is stored is provided inside the connector portion 14, but it is not limited to the connector portion 14. For example, the EEPROM 16 in which the scope ID is stored may be provided in the operation portion (the portion to be gripped by a user) provided with the operation switch 13, or may be provided on the insertion portion distal end. In addition, in a case of the configuration that the camera head is connected to the video processor 4, the EEPROM 16 in which the scope ID is stored may be provided inside a head portion connected to the eyepiece portion of the optical type endoscope and including a built-in image pickup device.

The light source device 3 includes an operation panel 20 for performing various kinds of operations such as adjustment of a light quantity, a light source 21 such as a lamp configured to generate the illumination light, and a converging lens 22 configured to converge the illumination light from the light source 21 to an incident end face of the light guide 12.

Note that the light source 21 of the light source device 3 is configured by a lamp or the like, but is not limited to the lamp, and may be configured by a semiconductor light emitting element (semiconductor light source) such as an LED or a laser diode. In addition, in the case of using the semiconductor light source, a semiconductor light source which emits white light may be used, or semiconductor light sources may be provided for respective color components of R (red), G (green) and B (blue) for example and the white light may be obtained by multiplexing light of the respective color components emitted from the semiconductor light sources. Further, the semiconductor light source may be configured to be provided on the insertion portion distal end of the endoscope 2.

The video processor 4 as a signal processor is configured including the connector 23 connected with the electric connector 14a of the endoscope 2, the control portion 24 such as a CPU configured to drive and control the image pickup device 11 of the endoscope 2 through the connector 23, an operation panel 25 for performing various kinds of operations and settings, a memory 26 configured to store various kinds of information, and a video processing unit 27 configured to execute the predetermined signal processing on image pickup signals from the image pickup device 11 through the connector 23.

The video processing unit 27 is configured including an NR processing circuit 28 configured to execute noise reduction (referred to as NR, hereinafter) to the video signals from the image pickup device 11, a white balance circuit 29 configured to execute white balance processing on output of the NR processing circuit 28, and a video processing circuit 30 configured to execute predetermined video signal processing such as color correction on output of the white balance circuit 29 and output the output to the monitor 5.

Figure 2:
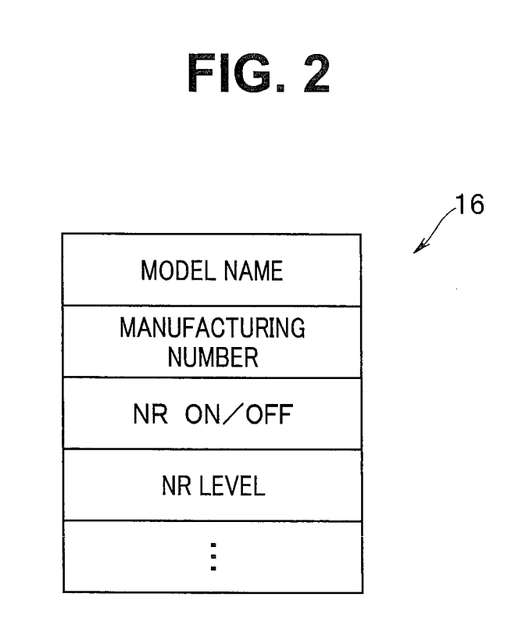
FIG. 2 is a diagram for describing one example of a scope ID stored in an EEPROM 16.

Here, the scope ID stored in the EEPROM 16 will be described. FIG. 2 is a diagram for describing one example of the scope ID stored in the EEPROM 16.

As illustrated in FIG. 2, the scope ID stored in the EEPROM 16 is information such as a model name, a manufacturing number, ON/OFF of the NR, and a level of the NR. The EEPROM 16 configures a data holding portion configured to hold data according to a kind of the image pickup device 11.

The information on the ON/OFF of the NR and the level of the NR stored in the EEPROM 16 is optimum data according to the kind of the image pickup device 11 of the endoscope 2. Note that, in the case where the NR is OFF, the information on the level of the NR may not be provided.

The control portion 24 of the video processor 4 communicates with the control circuit 17 of the endoscope 2, and instructs read of the scope ID stored in the EEPROM 16. When an instruction to read the scope ID is transmitted from the control portion 24, the control circuit 17 reads the scope ID, that is, the information on the model name, the manufacturing number, the ON/OFF of the NR and the level of the NR or the like, from the EEPROM 16, and transmits the scope ID to the control portion 24. In this way, the control portion 24 configures a data acquisition portion configured to acquire the data from the EEPROM 16.

The control portion 24 as a noise reduction processing setting portion sets the ON/OFF of the NR to the NR processing circuit 28, based on the information on the ON/OFF of the NR in the scope ID read from the EEPROM 16. In addition, in the case where the NR is set to be ON, the control portion 24 sets the level (strength) of the NR to be executed in the NR processing circuit 28, based on the information on the level of the NR.

Thus, the NR processing circuit 28 as a noise reduction processing portion executes or does not execute the NR to the image pickup signals from the image pickup device 11, according to the setting from the control portion 24. In addition, in the case of executing the NR, the NR processing circuit 28 executes the NR at the level according to the setting from the control portion 24.

Figure 3:
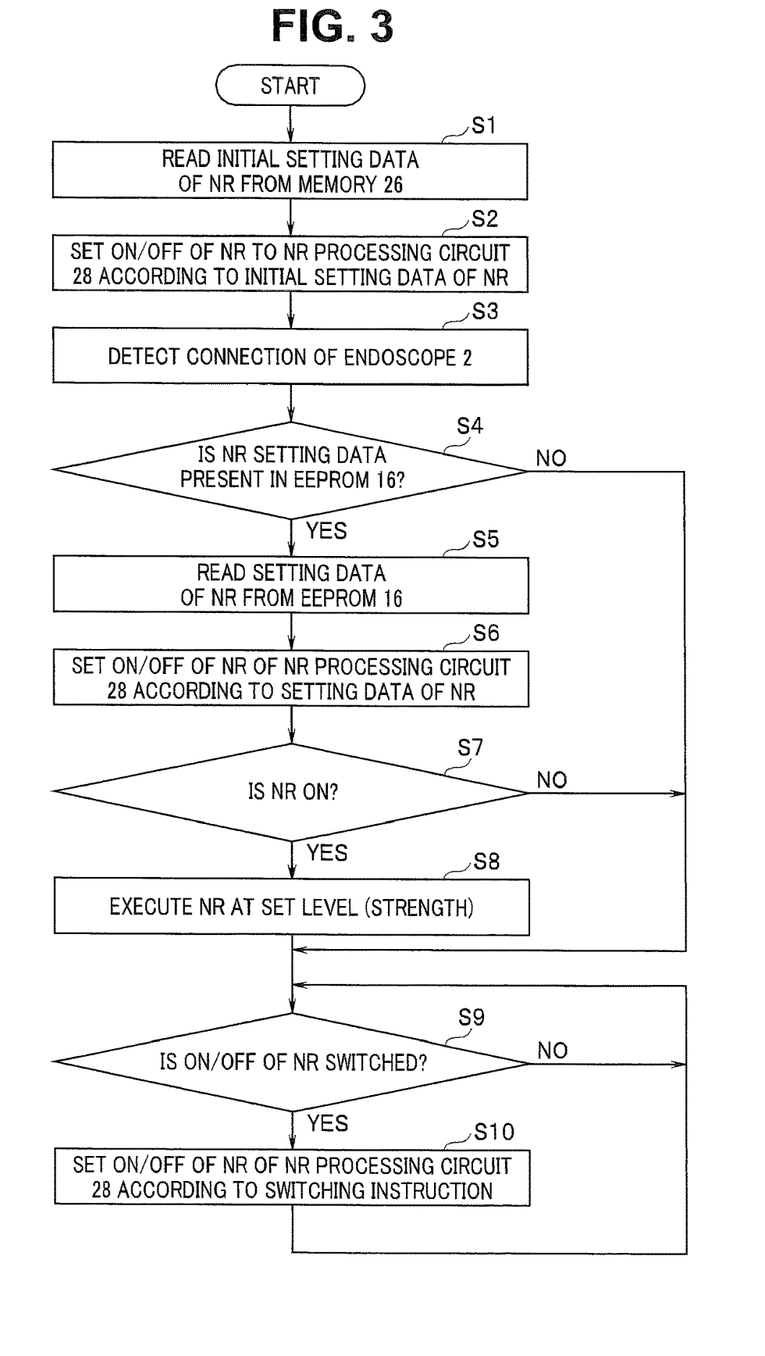
FIG. 3 is a flowchart for describing an example of a flow of setting processing of NR.

Next, setting processing of the NR in the endoscope system configured in this way will be described. FIG. 3 is a flowchart for describing an example of a flow of the setting processing of the NR.

When a power source of the video processor 4 is turned ON, the control portion 24 reads initial setting data of the NR from the memory 26 (step S1). The initial setting of the NR is set by a user and stored in the memory 26. The user can change the initial setting of the NR, using the operation switch 13 of the endoscope 2, the keyboard 6 connected to the video processor 4, or the operation panel 25 provided on the video processor 4, for example.

Next, the control portion 24 sets the ON/OFF of the NR to the NR processing circuit 28 according to the read initial setting data of the NR (step S2). Next, the control portion 24 detects the connection of the endoscope 2 (step S3), and determines whether or not setting data of the NR is present in the EEPROM 16 (step S4). At the time, the control portion 24 determines whether or not the setting data of the NR is present in the EEPROM 16 by communicating with the control circuit 17 of the memory portion 15 of the endoscope 2.

In the case where the control portion 24 determines that the setting data of the NR is not present in the EEPROM 16, it is NO, and the processing advances to step S9. On the other hand, in the case where the control portion 24 determines that the setting data of the NR is present in the EEPROM 16, it is YES, and the control portion 24 reads the setting data of the NR from the EEPROM 16 (step S5). Then, the control portion 24 sets the ON/OFF of the NR processing circuit 28 according to the read setting data (step S6).

Next, the control portion 24 determines whether or not the NR is ON (step S7). In the case where the control portion 24 determines that the NR is not ON, it is NO, and the processing advances to step S9. On the other hand, in the case where the control portion 24 determines that the NR is ON, it is YES, and the NR processing circuit 28 executes the NR at the set level (strength) (step S8).

Next, the control portion 24 determines whether or not the ON/OFF of the NR is switched (step S9). The video processor 4 is configured such that the ON/OFF of the NR can be switched by the user even after the NR is set in this way. The ON/OFF of the NR can be switched by the operation switch 13, the keyboard 6, or the operation panel 25, for example.

In the case where the control portion 24 determines that the ON/OFF of the NR is not switched, it is NO, the processing returns to step S9, and the similar processing is repeated. On the other hand, in the case where the control portion 24 determines that the ON/OFF of the NR is switched, it is YES, and the control portion 24 sets the ON/OFF of the NR of the NR processing circuit 28 according to a switching instruction (step S10). Thereafter, the processing returns to step S9, and the similar processing is repeated. Then, when the power source of the video processor 4 is turned OFF, the setting processing of the NR in FIG. 3 is ended.

As described above, in the endoscope system 1, the data of the optimum NR according to the kind of the image pickup device 11 of the endoscope 2 is stored in the EEPROM 16 inside the endoscope 2. The video processor 4 reads the data of the optimum NR according to the kind of the image pickup device 11 from the EEPROM 16 when the endoscope 2 is connected, and sets the ON/OFF of the NR and the level (in the case where the NR is ON) to the NR processing circuit 28. Thus, in the NR processing circuit 28, the optimum NR according to the kind of the loaded image pickup device 11 of the connected endoscope 2 can be executed.

Therefore, according to the endoscope system of the present embodiment, the optimum noise reduction processing can be executed according to the kind of the image pickup device.

Second Embodiment

Next, a second embodiment will be described.

Figure 4:
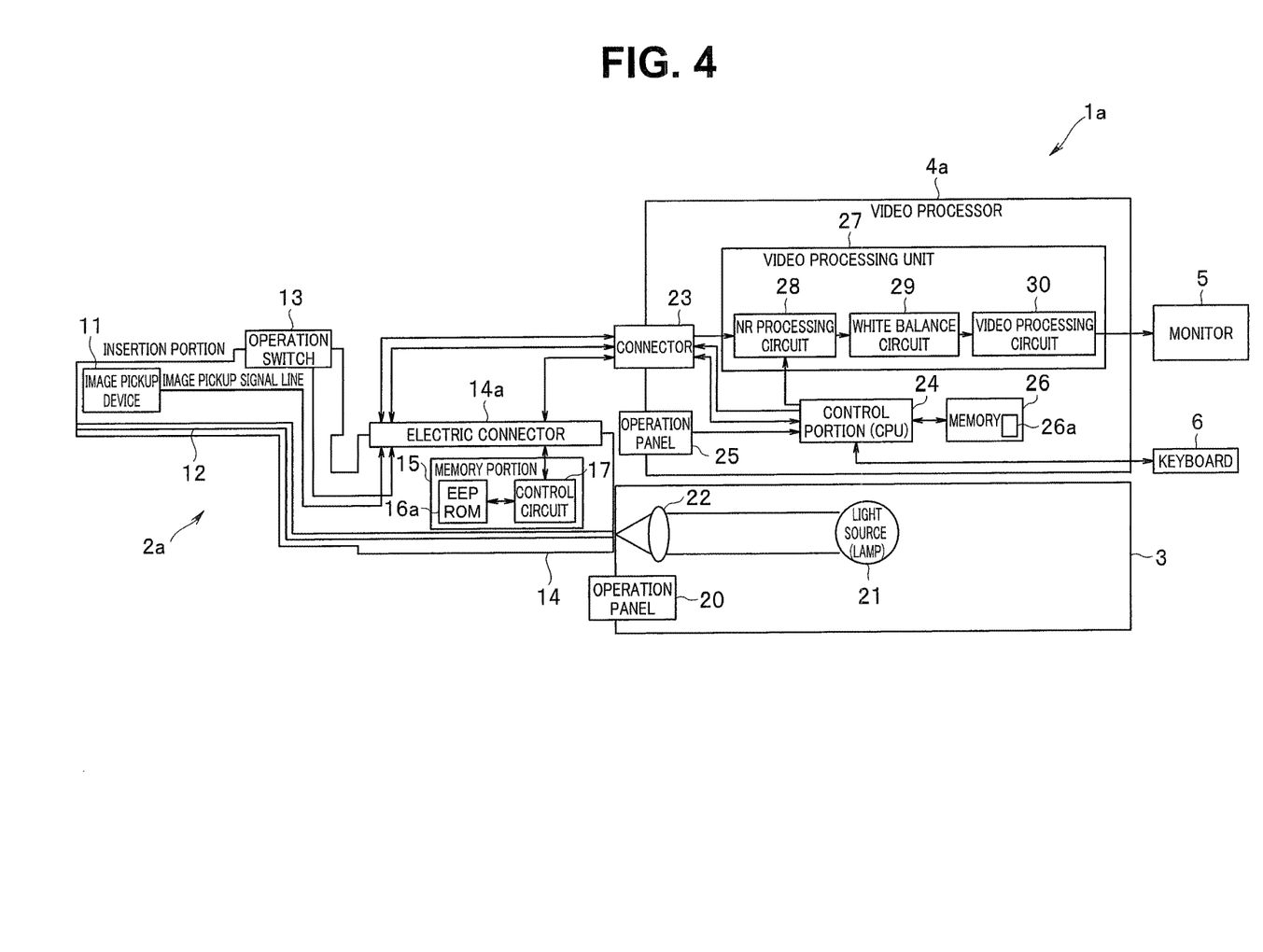
FIG. 4 is a diagram illustrating a configuration of an endoscope system relating to a second embodiment.

FIG. 4 is a diagram illustrating a configuration of an endoscope system relating to the second embodiment. Note that, in FIG. 4, for components similar to those in FIG. 1, same signs are attached and descriptions are omitted.

An endoscope system 1a is configured using an endoscope 2a and a video processor 4a respectively instead of the endoscope 2 and the video processor 4 in FIG. 1. The endoscope 2a is configured using an EEPROM 16a instead of the EEPROM 16 in FIG. 2. In addition, the video processor 4a is configured with a table 26a added to the memory 26 in FIG. 1.

Figure 5:
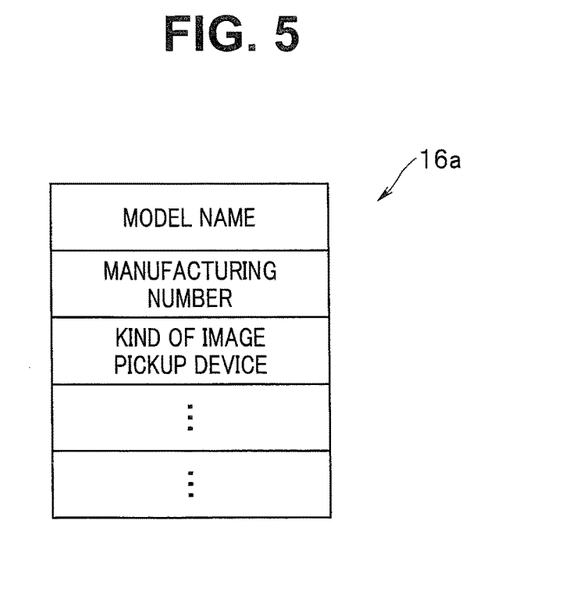
Figure 6:
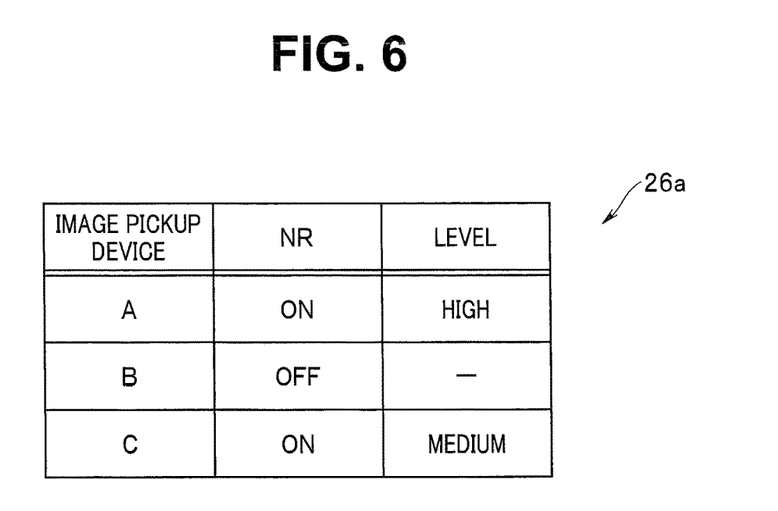

FIG. 5 is a diagram for describing one example of the scope ID stored in the EEPROM 16a, and FIG. 6 is a diagram for describing one example of the setting information on the NR stored in the table 26a.

As illustrated in FIG. 5, the scope ID stored in the EEPROM 16a configuring the data holding portion is the information on the model name, the manufacturing number and the kind of the image pickup device 11 or the like. In this way, in the EEPROM 16a, the information on the ON/OFF of the NR and the level of the NR in the EEPROM 16 in FIG. 2 is not stored.

On the other hand, as illustrated in FIG. 6, in the table 26a, the information on the kind of the image pickup device 11 and the ON/OFF of the NR is made to correspond. Further, in the case where the NR is ON, in addition to the information on the kind of the image pickup device 11 and the ON/OFF of the NR, the information on the level of the NR is made to correspond. For example, in the case where the kind of the image pickup device 11 is "A", the NR is "ON" and the level of the NR is "High". Note that, in the present embodiment, while the setting of the NR is configured to be changed according to the kind of the image pickup device 11, the setting of the NR may be configured to be changed according to the kind of the endoscope 2, for example.

When the endoscope 2a is connected to the video processor 4a, the control portion 24 reads the scope ID from the EEPROM 16a, and discriminates the kind of the image pickup device 11. Then, the control portion 24 refers to the table 26a, and sets the ON/OFF of the NR and the level (in the case where the NR is ON) of the NR of the corresponding image pickup device 11 to the NR processing circuit 28. The NR processing circuit 28 executes the NR by the ON/OFF of the NR and the level (in the case where the NR is ON) of the NR set in this way. The other configurations and operations are similar to those of the first embodiment.

According to the endoscope system 1a configured in this way, similarly to the first embodiment, the optimum noise reduction processing can be executed according to the kind of the image pickup device.

Modification of Second Embodiment

Next, a modification of the second embodiment will be described.

In the second embodiment, the video processor 4a reads and acquires the information on the kind of the image pickup device 11 stored in the EEPROM 16a of the endoscope 2, but is not limited to the configuration. For example, the video processor 4a may be configured to identify the kind of the image pickup device 11 by a combination of signals outputted from a plurality of detection pins provided in the endoscope 2a. In this case, the plurality of detection pins provided in the endoscope 2a hold the data according to the kind of the image pickup device 11. In this way, the detection pins configure the data holding portion configured to hold the data according to the kind of the image pickup device 11.

The detection pins are connected to the power source or ground, the detection pin connected to the power source outputs "1" (High), and the detection pin connected to the ground outputs "0" (Low). When the endoscope 2a is connected to the video processor 4a, the control portion 24 of the video processor 4a identifies the kind of the image pickup device 11, according to the combination of electronic data of "1" and "0" outputted from the detection pins.

When the kind of the image pickup device 11 is identified, similarly to the second embodiment, the control portion 24 refers to the table 26a, and sets the NR according to the kind of the image pickup device 11 to the NR processing circuit 28. The other configurations and operations are similar to those of the second embodiment.

Therefore, according to the endoscope system 1a of the modification, similarly to the second embodiment, the optimum noise reduction processing can be executed according to the kind of the image pickup device.

Note that, for individual steps in the flowchart in the present description, an execution order may be changed, the plurality of steps may be simultaneously executed, or the steps may be executed in different orders for each execution, unless contrary to natures of the steps.

The present invention is not limited to the embodiments described above, and various changes and modifications or the like are possible without changing the gist of the present invention.

What is claimed is:

1. An endoscope system comprising:
   an endoscope comprising:
      an image pickup device configured to pick up an image of a subject and output a signal based on the image that is picked up; and
      a first memory configured to store information on a kind of the image pickup device; and
   a signal processor to which the endoscope is attachably and detachably connected, wherein the signal processor is configured to:
      acquire the information on the kind of the image pickup device from the first memory when the endoscope is connected to the signal processor;
      reference a second memory storing, in a table, the information on the kind of the image pickup device in relation to execute/not execute information on whether to execute or not execute a noise reduction processing;
      set a processing content of the noise reduction processing comprising setting whether to execute or not execute the noise reduction processing, based on the execute/not execute information; and
      execute the noise reduction processing on the signal outputted from the image pickup device, based on the processing content set.

2. The endoscope system according to claim 1,
   wherein the second memory stores, in the table, the information on the kind of the image pickup device in relation to, in a case where the information on the kind of the image pickup device is stored in relation to information to execute the noise reduction processing, level information on a level of the noise reduction processing, and
   wherein the signal processor is configured to:
      set the processing content of the noise reduction processing comprising setting a level of the noise reduction processing, based on the level information; and
      execute the noise reduction processing on the video signal based on the processing content set.

3. The endoscope system according to claim 1,
   wherein the first memory comprises a detection pin configured to store the information on the kind of the image pickup device.

* * * * *